United States Patent
Poncin et al.

(10) Patent No.: US 6,989,438 B2
(45) Date of Patent: Jan. 24, 2006

(54) PROCESS FOR THE PURIFICATION OF EPI-HNE PROTEINS

(75) Inventors: Alain Poncin, Boncelles (BE); François Saudubray, Preverenges (CH); Anne Bokman, Martigny (CH)

(73) Assignee: Debiopharm S.A., (FR)

( * ) Notice: Subject to any disclaimer, the term of this patent is extended or adjusted under 35 U.S.C. 154(b) by 113 days.

(21) Appl. No.: 10/363,527

(22) PCT Filed: Aug. 30, 2001

(86) PCT No.: PCT/EP01/10727

§ 371 (c)(1),
(2), (4) Date: Mar. 3, 2003

(87) PCT Pub. No.: WO02/20613

PCT Pub. Date: Mar. 14, 2002

(65) Prior Publication Data

US 2004/0259223 A1    Dec. 23, 2004

(30) Foreign Application Priority Data

Sep. 4, 2000 (EP) .................................. 00203049
Oct. 31, 2000 (EP) .................................. 00403029
Jul. 10, 2001 (EP) .................................. 01202655

(51) Int. Cl.
*C07K 1/18* (2006.01)
*C12N 9/64* (2006.01)
*C12N 15/09* (2006.01)

(52) U.S. Cl. .................. 530/412; 530/416; 530/418; 435/226; 435/69.2

(58) Field of Classification Search ......... 435/46–69.2, 435/226; 514/1–19; 530/412, 416, 418
See application file for complete search history.

(56) References Cited

FOREIGN PATENT DOCUMENTS

WO    WO96/20278    12/1995
WO    WO9620278    *  7/1996

* cited by examiner

*Primary Examiner*—Karen Cochrane Carlson
*Assistant Examiner*—Marsha Tsay
(74) *Attorney, Agent, or Firm*—DLA Piper Rudnick Gray Cary US LLP

(57) ABSTRACT

The present invention concerns a process for the purification of EPI-HNE proteins, from the culture medium of a host strain for the expression of said proteins, comprising the steps of: (a) passing a derived part of the culture medium over an expanded bed of cationic exchange adsorbent or a mechanically and chemically inert micromembrane, in order to recover an eluate, (b) optionally conducting chromatographic separation of proteins, according to their hydrophobicity, on the resulting eluate, (c) passing the resulting eluate over a cationic exchange column, (d) optionally filtering the resulting medium such as to obtain a sterile filtrate, and optionally further comprising the step of (e) causing precipitation of EPI-HNE in a crystallised form and recovering the protein crystals.

18 Claims, No Drawings

PROCESS FOR THE PURIFICATION OF EPI-HNE PROTEINS

The present invention concerns a novel process for the purification of EPI-HNE proteins.

International Patent Application WO 96/20278 to Ley et al. describes a number of genetically engineered novel proteins which inhibit human neutrophil elastase (hNE). As indicated in the above-cited patent application, human neutrophil elastase (also known as human leukocyte elastase) is one of the major neutral proteases of the azurophil granules of polymorphonuclear leukocytes. This enzyme is involved in the elimination of pathogens, and in connective tissue restructuring.

The principal systemic inhibitor of hNE is the α-1-protease inhibitor, formerly known as α1 antitrypsin. In a certain number of pathological situations (hereditary disorders, emphysema, cystic fibrosis, Adult Respiratory Distress Syndrome ARDS, Chronic Obstructive Pulmonary Disease COPD), this inhibitor is either not present in sufficient amounts in the bloodstream or is inactivated, leading to uncontrolled elastolytic activity of hNE, which causes extensive destruction of lung tissue.

WO 96/20278 thus proposes novel proteins which are stable, non-toxic, highly efficacious inhibitors of hNE. These inhibitors form part of a group of inhibitors derived from a Kunitz-type inhibitory domain found in basic pancreatic trypsin inhibitor (BPTI) or a protein of human origin, namely the light chain of human Inter-α-trypsin inhibitor (ITI). They are, inter alia, EPI-HNE-1, EPI-HNE-2, EPI-HNE-3 and EPI-HNE-4. The inhibitors of WO 96/20278 are produced by biotechnological methods and contain modified DNA sequences, with respect to the biological Kunitz domains, which render them highly potent. One of these inhibitors, EPI-HNE-4, is of particular interest.

WO 96/20278 describes preparation of *Pichia pastoris* production systems for hNE inhibitors EPI-HNE1, EPI-HNE-2, EPI-HNE-3 and EPI-HNE-4, protein production and purification (see in particular Examples 10–15).

Yeast *Pichia pastoris* mutant strain GS115 containing a non functional histidinol dehydrogenase gene (his4) was transformed by expression plasmids comprising a sequence encoding the *S. cerevisiae* mating factor alpha prepro peptide fused directly to the amino terminus of the desired hNE inhibitor, under control of the upstream inducible *P. pastoris* aox1 gene promoter and the downstream aox1 transcription termination and polyadenylation sequences. The expression plasmids were linearized by SacI digestion and the linear DNA was incorporated by homologous recombination into the genome of the *P. pastoris* strain GS115 by spheroplast transformation, selection for growth in the absence of added histidine and screening for methanol utilization phenotype, secretion levels and gene dose (estimated by Southern Blot). Strains estimated to have about four copies of the expression plasmid integrated as a tandem array into the aox1 gene locus were thus selected.

Cultures of selected strains were first grown in batch mode with glycerol as the carbon source, then following exhaustion of glycerol grown in glycerol-limited feed mode to further increase cell mass and derepress the aox1 promoter and finally in methanol-limited feed mode. During the latter phase the aox1 promoter was fully active and the protein was secreted into the culture medium.

Ley et al. then indicate that the proteins were purified using standard biochemical techniques, the specific purification procedure varying with the specific properties of each protein. Briefly, the culture medium was centrifuged, the supernatant was subjected to microfiltration and subsequently to ultrafiltration, possibly to diafiltration, and then the protein was recovered by ammonium sulfate precipitation and ion exchange chromatography.

Specific production and purification procedures are described in WO 96/20278 only for EPI-HNE2 and EPI-HNE3, the overall purification yield starting from a culture medium containing 720 mg/l and 85 mg/l being about 30% and 15%, respectively, for a purity for each of those proteins of over 95% as assessed by silver-stained high-resolution PAGE analysis. The purified EPI-HNE3 is disclosed to be substantially free of a alternatively-processed form of this protein having an amino extension of 7 to 9 amino acid residues and representing about 15–20% of the hNE inhibitory activity.

EPI-HNE1 and EPI-HNE4 are only taught as being produced and purified in a manner analogous to EPI-HNE2 and EPI-HNE3, without any disclosure of the specific purification procedure, the purification yield or the purity of the purified protein.

The procedures for the purification of EPI-HNE proteins disclosed in WO 96/20278 are not suited for obtaining amounts of purified proteins of acceptable pharmaceutical quality on an industrial scale. Indeed the sucession of centrifugation, microfiltration and ultrafiltration steps cannot be performed in an economically viable manner on a large scale and leads to insufficient yields. Besides, as shown by the applicant in Example 1, the purified protein is not separated from pharmaceutically unacceptable contaminants such as green fluorescent pigments secreted by *P. pastoris*.

The problem addressed by the invention is therefore to develop a process for the purification of an EPI-hNE protein from the culture medium of a host strain capable of expressing that protein, which does not have the above-mentioned drawbacks.

The above problem is solved by the invention as defined in the appended claims.

The process of the invention allows to purify large quantities of an EPI-HNE protein from the culture medium of a host strain expressing that protein, with an overall yield of at least about 40%, preferably at least 60%, to a degree acceptable for pharmaceutical uses.

The invention concerns a process for the purification of EPI-HNE proteins, from the culture medium of a host strain for the expression of said proteins, comprising the steps of:

(a) passing a derived part of the culture medium over an expanded bed of cationic exchange adsorbent or a mechanically and chemically inert micromembrane, in order to recover an eluate, (b) optionally conducting chromatographic separation of proteins, according to their hydrophobicity, on the resulting eluate, (c) passing the resulting eluate over a cationic exchange column, (d) optionally filtering the resulting medium such as to obtain a sterile filtrate The host strains used for the expression of the EPI-HNE proteins may be selected among suitable strains of any prokaryotic or eukaryotic organisms transformed by a vector for the expression of said proteins. Preferably, the host strain is selected from the group consisting of bacteriae such as *Escherichia Coli, Streptomyces* or *Lactococcus* and yeast such as *Saccharomyces cerevisiae, Schisaosaccharomyces pombe, Yarrovia lipilitica, Hansenula polymorpha, Kluyveromyces lactis, Pichia methanolica* and *Pichia pas-*

*toris*, which are capable of expressing high levels of a recombinant protein. Even more preferably, the host strain is *Pichia pastoris*.

The expression "derived part of the culture medium" has a specific meaning in the context of the present invention, as indicated hereafter.

When the host strain is capable of secreting the protein outside the cell, the derived part of the culture medium in step (a) is the culture broth.

When the host strain expresses the protein inside the cell, e.g. in the periplasm, the derived part of the culture medium in step (a) is the lysis product thereof.

Preferably the above process comprises the further step of:

(e) causing precipitation of EPI-HNE in a crystallised form and recovering the protein crystals.

Step (a) is an expanded bed adsorption step conducted on a cationic exchange adsorbent, well known in the art (see for example, M. Hansson et al., 1994, Biotechnol. 12, pp. 285–288) or a filtration step on a mechanically and chemically inert micromembrane.

The cationic exchange adsorbent may be based on crosslinked agarose or cross-linked sepharose, modified through the inclusion of an inert core material, such as crystalline quartz, to provide the required high density for stable bed expansion, preferably from 1.1 to 1.5 g/ml, or zirconium having a higher density between about 3.5 mg/ml, which allows a higher flow rate, and by attachment of surface cationic functional groups, notably strong cationic groups such as sulfonate. The particles may be spherical, with a mean particle size of 100–300 µm, preferably from 180–220 µm. A suitable cationic exchange adsorbent is Streamline SP or Streamline SPXL from Amersham-Pharmacia.

In a preferred embodiment of the invention, the passage over an expanded bed is performed as follows:

Ten liters of chromatographic matrix (Streamline SP from Amersham-Pharmacia) is equilibrated in 50 mM ammonium acetate pH 3.5 and fluidized in the same buffer to 30 l at 300 cm/h. The system allows the direct loading of the collected culture medium, thus avoiding the further steps of centrifugation, microfiltration and ultrafiltration of the prior art, and allowing increase in yields. After loading, the column is washed in the 10 mM ammonium acetate pH 3.5 to obtain an absorption at 280 nm below 0.05. The beads are packed to 10 l and EPI-HNE-4 is recovered by washing the column in 1 M ammonium acetate pH 4.5 buffer.

A mechanically and chemically inert micromembrane here means a microfiltrating medium which has a wide pH compatibility, preferably at least between 3 and 14, allows a high flux of filtrate and is able to withstand high burst pressure, preferably at least 10 bars, in particular at least 50 bars, and backpulsing. Commercially available such membranes are generally made of ceramics. Examples of such membranes are Membralox® (J.M. Separations), Carbosep®/Kerasep™ (Rhodia) and ProCell™ Large Process Scale Cartridge (A/G Technology Corporation).

Optional step (b) is a hydrophobic interaction or reverse phase chromatography step which allows to separate a mixture of proteins according to their hydrophobicity. That step may be useful when fermentation is performed on a large scale (over 1 cubic meter) and possibly additional contaminants may be present.

Hydrophobic interaction or reverse phase chromatography is well known in the art and described notably in "Protein purification, Second edition Principles, High resolution Methods and applications", Ed. J. C. Janson and. L. Rydén, pp 239–282.

A hydrophobic interaction chromatography step is preferable since it can be performed without using organic solvents.

A suitable matrix is a polymer such as polystyrene, polystyrene-divinylbenzene crosslinked methacrylate, modified methacrylate, polyacrylamide, crosslinked agarose or crosslinked sepharose, which carries a ligand having a hydrophobicity between the hydrophobicity conferred by a C2 alkyl group and the hydrophobicity conferred by a C8 alkyl group. Examples of such ligands are ethyl, propyl, isopropyl, butyl, isobutyl, tertiobutyl, pentyl, isopentyl, hexyl, phenyl, isopropanol, isobutanol, C4–C6 ether. Phenyl is preferred.

Examples of suitable matrices are Toyopearl hexyl 650C (modified methacrylate with hexyl ligand), Toyopearl ether 650M (modified methacrylate with C5-ether ligand), Toyopearl butyl 650M (modified methacrylate with butyl ligand) and Toyopearl phenyl 650M (modified methacrylate with phenyl ligand), available from Tosohaas; Resource ETH (polystyrene-divinylbenzene with ethyl ligand), Resource ISO (polystyrene-divinylbenzene with isopropanol ligand), Resource Phe (polystyrene-divinylbenzene with phenyl ligand), Phenyl-sepharose Fast Flow (crosslinked sepharose with phenyl ligand), available from Amersham-Pharmacia; Macroprep t-butyl (crosslinked methacrylate with t-butyl ligand) and Macroprep Phenyl (crosslinked methacrylate with phenyl ligand) available from Bio-Rad.

Most preferably the matrix is Phenyl-sepharose Fast Flow from Amersham-Pharmacia (rigid matrix of 45–165 µm beads of crosslinked sepharose with phenyl ligand).

Where step (b) is a reverse phase chromatography step a suitable matrix is a polymer such as polystyrene, polystyrene-divinylbenzene, crosslinked methacrylate, modified methacrylate, which carries no ligand or a ligand having a hydrophobicity greater than that conferred by a C10 alkyl group.

Examples of suitable matrices are CG300-M (polystyrene-divinylbenzene), CG161-M (polystyrene-divinylbenzene), available from Tosohaas; Resource 15RP (polystyrene-divinylbenzene), Resource RPC (polystyrene-divinylbenzene), available from Amersham-Pharmacia; Macroprep High S C18 (crosslinked methacrylate with C18 ligand) available from Bio-Rad; Poros 50R1 et Poros 50R2 (polystyrene-divinylbenzene), available from Perseptive Biosystems.

In a preferred embodiment of the process according to the invention, the matrix upon which the reverse phase chromatography is conducted is constituted by synthetic hydrophobic beads. Preferably, the matrix is a polystyrene-divinylbenzene matrix, preferably with beads of 60–90 µm, more preferably 75 µm, and with a pore size greater than 150 Å, preferably a pore size of 300 Å.

Most preferably, the matrix is a CG 300 M matrix, available from TosoHaas (polystyrene matrix, 75 µm beads with average pore size of 300 Å).

In the process according to the present invention the main contaminants after the expanded bed chromatography or microfiltration, are the pigments from the host cells, which include polyphenols and degradation products thereof.

The cationic exchange column of step (c) is selected such that the EPI-HNE protein does not precipitate while passing through the column. In order to obtain a high yield, this step is preferably conducted at a pH between 1.8 and 5.0, preferably between 2.0 and 3.0. The elution is performed under conditions such as to obtain a high concentration of EPI-HNE (over 10 mg/ml) and low ionic strength (less than 25 mS/cm). Such an elution might be obtained by "displacement chromatography" using a polycation such as polyethyleneimine, polylysine, polyargininine or any other polymer, such as e.g. polyvinylpyrrolidone (PVP), which contains a high density of positive charges at a pH between 1.8 and 5. The same result may be obtained by loading a diluted peak after step (a) or (b) on a weak cation exchanger at a pH between 4.5 and 5.0 and by elution at pH 2.0 since the weak cation exchanger possess no anionic charge at such acidic pH and retained no more cationic proteins.

Examples of a suitable matrix for the cationic exchange column include Macroprep High S matrix (rigid matrix based on cross-linked methacrylate carrying sulphonate surface groups) from BioRad; S. Sepharose Fast Flow (crosslinked agarose carrying sulphonate groups) and Carboxymethyl Sepharose (crosslinked sepharose carrying carboxymethyl groups) from Amersham-Pharmacia.

Step (c) is a conventional cationic exchange step which allows to concentrate the EPI-HNE protein to allow its high yield and high speed crystallisation if step (e) is used and, if an organic solvent is used during step (b), to eliminate traces thereof which are not acceptable for a pharmaceutical.

The aim of optional step (d) is to eliminate all microorganisms such as e.g. bacteriae or yeast. This step is of particular importance when the conditions subsequently used are capable of causing substantial growth of microorganisms, e.g. when step (e) is performed over a time period over 3 hours. The filtration under sterile conditions is performed under conditions well known in the art, for example at 0.22 $\mu$m.

In step (e) the precipitation of EPI-HNE in a crystallised form is suitably performed in an aqueous vehicle at a pH comprised between 3.0 and 8.0, preferably 4.0 and 6.0, most preferably at a pH of 4.0 to 5.0, the concentration of the EPI-hNE protein in the aqueous vehicle being comprised between 1 and 80 mg/ml, preferably between 2 and 50 mg/ml.

Step (e) is preferably performed using cycles of crystallisation/sonication. The latter indeed dramatically increase the kinetics of precipitation, thereby substantially reducing the time necessary for carrying out step (e).

The aqueous vehicle is suitably a saline solution having an iso-osmotic pressure. The saline solution may comprise sodium or ammonium acetate and sodium or ammonium chloride, or sodium or ammonium citrate.

The term "crystallised form" of EPI-HNE here means an insoluble form of that protein having a rod-like structure and a size mainly below 10 $\mu$m.

The crystals of EPI-HNE are recovered by centrifugation or fitration.

The recovered crystals may be directly suspended in a pharmaceutically acceptable buffer or freeze-dried in a suitable buffer such as ammonium bicarbonate 10 mM or spray dried into an aerosol powder.

The EPI-HNE proteins to be purified according to the process of the present invention may be selected from the group consisting of EPI-HNE-1, EPI-HNE-2, EPI-HNE-3, and EPI-HNE-4. EPI-HNE-4 is preferred.

The invention will be illustrated by the following examples.

EXAMPLE 1

Purification of EPI-HNE4 Using a Slight Modification of the Method Disclosed for Purifying EPI-HNE3 in Example 13 of WO 96/20278 (Comparative Example)

Yeast Production System

The hNE inhibitors are produced as secreted proteins in the culture supernatants of high cell density *Pichia pastoris* strain GS115 fermentations. Expression plasmids are constructed by ligating synthetic DNA sequences encoding the *Saccharomyces cerevisiae* mating factor α prepropeptide directly to the 5'-terminus of synthetic DNA encoding the desired hNE inhibitor. This fusion gene is sandwiched between an upstream inducible *P. pastoris* aox1 gene promoter and downstream aox1 gene transcription termination and polyadenylation sequences that are carried on a plasmid that also encodes a *S. cerevisiae* his4 gene. Linearized expression-plasmid DNA is incorporated by homologous recombination into the genome of the *P. pastoris* strain GS115 by spheroplast transformation. Regenerated spheroplasts are selected for growth in the absence of added histidine. Individual isolates are screened for methanol utilization phenotype (mut +), secretion levels, and gene copy number. Strain PEY-53 secreting a high level of EPI-HNE-4 was thus selected. This strain is estimated by Southern analysis of genomic DNA to contain four copies of expression plasmid DNA integrated into the aox1 gene locus.

Protein Production

*P. pastoris* strain PEY-53 are grown in mixed-feed fermentations similar to the procedure described in WO 96/20278, with the difference that pressurized air is used instead of purified oxygen. Briefly, cultures are first grown in batch mode with glycerol as the carbon source. After exhaustion of glycerol, the cultures are grown for about four hours in glycerol-limited feed mode to further increase cell mass and to derepress the aox1 promoter. In the final production phase, the cultures are grown in methanol-limited feed mode. During this phase, the aox1 promoter is fully active and the hNE inhibitors are secreted into the conditioned medium (C.M.) The final concentration of EPI-HNE-4 in the PEY-53 fermentation C.M. was about 600 mg/L as determined by SDS-PAGE analysis.

The major molecular species produced by PEY-53 cultures is the properly processed EPI-HNE-4 protein. However, this strain also secretes about 5–20% of an alternatively-processed protein having slightly higher molecular weight Purification of EPI-HNE-4

2.5 l of the PEY-53 CM is harvested by centrifugation and the supernatant is 0.2$\mu$ microfiltered as described above. A 30 Kda ultrafiltration is performed on the 0.2$\mu$ filtrate, and when the retentate volume is reduced to about 250 ml, a diafiltration of the retentate is performed at a constant retentate volume (250 ml) for 60 min at a rate of 10 ml/min. The resulting final volume of 30 Kda filtrate is about 3 l.

Properly processed EPI-HNE-4 is purified substantially free of alternatively-processed form and other fermenter culture components by ion exchange chromatography on a polyacrylamide gel carrying sulfonate groups (Macroprep 50S Biorad). A 50 ml bed volume of Macroprep 50S is equilibrated with 10 mM sodium citrate pH 3.5, the 30 Kda ultrafiltration filtrate applied to the column (complete binding of EPI-HNE-4 to the column is confirmed by demonstrating the absence of hNE inhibitor activity in the column eluate), and the column washed with ten column volumes of 10 mM sodium citrate, pH 3.5. The column is then eluted with a gradient from 10 mM ammonium acetate pH3.5 to 1M ammonium acetate pH 3.5 in 30 column volumes. EPI-HNE4 is eluted at the end of the gradient as a single symmetric peak. The eluate is freeze-dried.

300 mg of purified active EPI-HNE4 were thus obtained from 2.5 l of CM corresponding to a yield of about 20%.

SDS-PAGE analysis showed a purity of the product over 95%. The main contaminant was a green fluorescent pigment.

EXAMPLE 2

Purification of EPI-HNE4 According to the Method of the Invention wherein Step (b) is a Hydrophobic Interaction Chromatography Step 100 l of the PEY-53 CM obtained as described in Example 1 were collected and passed over an expanded bed as follows: 10 l of chromatographic matrix (Streamline SP from Amersham-Pharmacia) is equilibrated in 50 mM ammonium acetate pH 3.5 and fluidized in the same buffer to 30 l at 300 cm/h. After loading, the column is washed in the 10 mM ammonium acetate pH 3.5 to obtain an absorption at 280 nm below 0.05. The beads are packed to 10 l and EPI-HNE-4 is recovered by washing the column in 1 M ammonium acetate pH 4.5 buffer.

Thus was obtained a 10 l solution containing about 60 g of proteins and pigments (as determined by spectrometric assay at 280 nm and by Coomassie protein assay). RP-HPLC (silica column Licrosphere 100RP from pharmacia/gradient of water+1% TFA and acetonitrile+1% TFA) showed that the amount of EPI-HNE4 was only about 30 g and the alternatively-processed form was not separated from the main form. The contamination by green contaminants is detectable.

The solution was sterile-filtered on a 22 µm filter (Millipack 200 from Millipore) before further purification.

Hydrophobic interaction chromatography was conducted by passing the above 10 l solution on a BioProcess (Pharmacia) system, using a phenyl-sepharose Fast Flow matrix from Pharmacia in a 15 l BPTG column from Pharmacia. The buffers used were A: sodium acetate 50 mM pH 4.5+1M NaCl, and B: sodium acetate 50 mM pH 4.5. The elution was performed in one step at 100% B with a flow rate of 300 cm/h.

The eluate contained about 15 g of purified EPI-HNE4 (as determined by spectrometric assay at 280 nm, Coomassie protein assay and biological activity assay).

RP-HPLC showed that the alternatively-processed form was not separated. No green pigment was detectable.

Cation exchange chromatography was then performed using a Bioprocess chromatographic system from Pharmacia. The matrix used was Macroprep High S matrix from BioRad (rigid matrix based on cross-linked methacrylate carrying sulphonate surface groups), in a 15 l BPG200 column from Pharmacia. The buffers used were A: ammonium acetate 10 mM pH 3.5, B: sodium acetate 50 mM pH 6.2 and C: 10 mM ammonium bicarbonate pH 7.8. A first elution in buffer B was used to separate the alternatively processed form. Elution was then performed by one step at 100% C with a flow rate of 300 cm/h.

The eluate contained about 12 g of purified EPI-HNE4 (as determined by spectrometric assay at 280 nm, Coomassie protein assay and biological activity assay), corresponding to an overall yield of the purification process of about 40%.

RP-HPLC showed less than 1.5% of the alternatively-processed form. No green pigment was detectable.

EXAMPLE 3

Purification of EPI-HNE4 According to the Method of the Invention wherein Step (b) is a Reverse Chromatography Step 100 l of the PEY-53 CM obtained as described in Example 1 were collected and passed over an expanded bed as follows: 10 l of chromatographic matrix (Streamline SP from Amersham-Pharmacia) is equilibrated in 50 mM ammonium acetate pH 3.5 and fluidized in the same buffer to 30 l at 300 cm/h. After loading, the column is washed in the 10 mM ammonium acetate pH 3.5 to obtain an absorption at 280 nm below 0.05. The beads are packed to 10 l and EPI-HNE-4 is recovered by washing the column in 1 M ammonium acetate pH 4.5 buffer.

Thus was obtained a 10 l solution containing about 60 g of proteins and pigments (as determined by spectrometric assay at 280 nm and Coomassie protein assay). RP-HPLC (silica column Licrosphere 100RP from Pharmacia/gradient of water+1% TFA and acetonitrile+1% TFA) showed that the amount of EPI-HNE4 was about 30 g and the alternatively-processed form was not separated from the correct form. The contamination by green contaminants is detectable.

The solution was sterile-filtered on a 22 µm filter (Millipack 200 from Millipore) before further purification.

Reverse phase chromatography was conducted by passing the above 10 l solution on a BioProcess (Pharmacia) system, using a CG-300 M matrix from Tosohaas in a 50 l BTSS column from Pharmacia. The buffers used were A: water+0.1% TFA, and B: acetonitrile+0.1% TFA. The column gradient was 25–45% B in 40 column volume and the flow rate was 450 cm/h.

The eluate contained about 30 g of purified EPI-HNE4 (as determined by spectrometric assay at 280 nm, Coomassie protein assay and biological activity assay).

RP-HPLC showed less than 2% of the alternatively-processed form. No green pigment was detectable.

Cation exchange chromatography was then performed using a Bioprocess chromatographic system from Pharmacia. The matrix used was Macroprep High S matrix from BioRad (rigid matrix based on cross-linked methacrylate carrying sulphonate surface groups), in a 0.5 l BPG100 column from Pharmacia. The buffers used were A: ammonium acetate 10 mM pH 3.5, and B: 10 mM ammonium bicarbonate pH 7.8. Elution was performed by step at 100% B and the flow rate was 300 cm/h.

The eluate contained about 25 g of purified EPI-HNE4 (as determined by spectrometric assay at 280 nm, Coomassie protein assay and biological activity assay), corresponding to an overall yield of the purification process of about 40%.

RP-HPLC showed less than 2% of the alternatively-processed form. No green pigment was detectable.

Only traces of acetonitrile were present.

These traces of acetonitrile were completely eliminated either by freeze-drying or by diafiltration.

EXAMPLE 4

Purification of EPI-HNE4 According to the Method of the Invention wherein Step (b) is a Reverse Chromatography Step and Step (e) is Used 100 l of the PEY-53 CM obtained as described in Example 1 were collected and passed over an expanded bed as follows: 10 l of chromatographic matrix (Streamline SP from Amersham-Pharmacia) is equilibrated in 50 mM ammonium acetate pH 3.5 and fluidized in the same buffer to 30 l at 300 cm/h. After loading, the column is washed in the 10 mM ammonium acetate pH 3.5 to obtain an absorption at 280 nm below 0.05. The beads are packed to 10 l and EPI-HNE-4 is recovered by washing the column in 1 M ammonium acetate pH 4.5 buffer.

Thus was obtained a 10 l solution containing about 60 g of proteins and pigments (as determined by spectrometric assay at 280 nm and Coomassie protein assay). RP-HPLC (silica column Licrosphere 100RP from pharmacia/gradient of water+1% TFA and acetonitrile+1% TFA) showed that the amount of EPI-HNE4 was about 30 g and the alternatively-processed form is not separated from the correct form. The contamination by green contaminants is detectable.

The solution was sterile-filtered on a 22 μm filter (Millipack 200 from Millipore) before further purification.

Reverse phase chromatography was Conducted by passing the above 10 l solution on a BioProcess (Pharmacia) system, using a CG-300 M matrix from Tosohaas in a 50 l BTSS column from Pharmacia. The buffers used were A: water+0.1% TFA, and B: acetonitrile+0.1% TFA. The column was washed in 25% B to was the green pigments and the unidentified coumpound thus in 60% B to eluate the EPI-hNE-4 protein. The flow rate was 450 cm/h.

The eluate contained about 25 g of purified EPI-HNE4 (as determined by spectrometric assay at 280 nm, Coomassie protein assay and biological activity assay).

RP-HPLC showed that the alternatively-processed form was conserved. No green pigment was detectable.

Cation exchange chromatography was then performed using a Bioprocess chromatographic system from Pharmacia. The matrix used was Macroprep High S matrix from BioRad (rigid matrix based on cross-linked methacrylate carrying sulphonate surface groups), in a 0.5 l XK50 column from Pharmacia. The buffers used were A: sodium acetate 10 mM pH 2.0, and B: 10 mM sodium acetate pH 2.0+Polyethylene imine 1%. Elution was performed by step at 100% B and the flow rate was 300 cm/h.

The eluate contained about 50 g of purified EPI-HNE4 (as determined by spectrometric assay at 280 nm, Coomassie protein assay and biological activity assay)

The eluate contained about 50 mg/ml of EPI-hNE-4 at low ionic strength (15 mS/cm).

The pH of this eluate was increased to pH 4.5 with sodium hydroxyde 1 M and allowed to crystallize overnight.

The crystals were recovered by centrifugation (30 min, 10 000 g) and resuspended in 10 mM ammonium bicarbonate buffer before freeze drying.

20 g of EPI-hNE-4 protein were thus recovered, corresponding to an overall yield of the purification process of about 66%.

RP-HPLC showed less than 5% of the alternatively-processed form. No green pigment nor any material absorbing at a wave length of 200 nm were detectable.

EXAMPLE 5

Purification of EPI-HNE4 According to the Method of the Invention wherein Optional Step (b) is Not Used and Step (e) is Used This example will highlight the advantage of using step (e). Since purification by crystallisation step (e) is very efficient in eliminating the green pigments, step (b) seems not to be necessary when step (e) is used.

The experimental conditions are the same as in Example 4, except for step (b) which is not used. In step (e), several cycles of sonication/crystallisation are introduced.

The amounts of EPI-HNE4 obtained after step (a), step (c) and step (e) for four runs of fermentation using different volumes of fermentation broth are set out in Table 1 below.

TABLE 1

| VOLUME OF FERMENTATION BROTH | EPI-HNE4 after fermentation (g) | After step (a) | After step (c) | After step (e) | Overall yield of purification % |
|---|---|---|---|---|---|
| 1 L | 0.3 | 0.29 | 0.32 | 0.18 | 60 |
| 10 L | 3 | 2.95 | 2.9 | 1.2 | 40 |
| 50 L | 5* | 5 | 5 | 2.8 | 56 |
| 100 L | 30 | 29.4 | 29.2 | 14 | 46 |

*The level of expression of EPI-HNE4 was exceptionally low (100 mg/L instead of 300 mg/L) due to the configuration of the 50 L fermentation used, not adapted to fermentation of yeast.

The invention claimed is:

1. Process for the purification of EPI-HNE proteins, from the culture medium of a host strain for the expression of said proteins, comprising the steps of:
   (a) passing a derived part of the culture medium over an expanded bed of cationic exchange adsorbent or a mechanically and chemically inert micromembrane, in order to recover an eluate,
   (b) optionally conducting chromatographic separation of proteins, according to their hydrophobicity, on the resulting eluate,
   (c) passing the resulting eluate over a cationic exchange column,
   (d) optionally filtering the resulting medium for obtaining a sterile filtrate
   (e) causing precipitation of EPI-HNE in a crystallised form and
   recovering the protein crystals.

2. Process according to claim 1, wherein step (c) is performed at a pH between 1.8 and 5.0.

3. Process according to claim 2, wherein the elution in step (c) is performed under conditions providing a high concentration of EPI-HNE and a low ionic strength.

4. Process according to claim 3, wherein the elution is obtained by displacement chromatography.

5. Process according to claim 1, wherein in step (e) precipitation of EPI-HNE in a crystallised form is conducted in an aqueous vehicle at a pH between 3.0 and 8.0.

6. Process according to claim 5, wherein the concentration of EPI-HNE in the aqueous vehicle is from 1 to 80 mg/ml.

7. Process according to claim 1, wherein step (e) is performed using cycles of crystallisation/sonication.

8. Process according to claim 1, wherein step (b) is a hydrophobic interaction chromatography step where the matrix is a polymer carrying a ligand having a hydrophobicity between the hydrophobicity conferred by a C2 alkyl group and the hydrophobicity conferred by a C8 alkyl group.

9. Process according to claim 8 wherein the matrix is a polymer carrying a ligand wherein the ligand is selected from the group consisting of ethyl, propyl, isopropyl, butyl, isobutyl, tert-butyl, pentyl, isopentyl, hexyl, phenyl, isopropanol, isobutanol, and C4–C6 ether.

10. Process according to claim 1, wherein step (b) is a reverse phase chromatography step conducted on a matrix composed of synthetic hydrophobic beads.

11. Process according to claim 10, wherein the matrix is a polystyrene-divinylbenzene matrix.

12. Process according to claim 1, wherein in step (d) the resulting medium is filtered for providing a sterile filtrate.

13. Process according to claim 1, wherein step (c) is performed at a pH between 2.0 and 3.0.

14. Process according to claim 1, wherein in step (e) precipitation of EPI-HNE in a crystallised form is conducted in an aqueous vehicle at a pH between 4.0 and 6.0.

15. Process according to claim 5, wherein the concentration of EPI-HNE in the aqueous vehicle is from 2 to 50 mg/ml.

16. Process according to claim 10, wherein the matrix is a polystyrene-divinylbenzene matrix, with beads of 75 µm, and with a pore size greater than 150 Å.

17. Process according to claim 10, wherein the matrix is a polystyrene-divinylbenzene matrix, with beads of 60–90 µm, and with a pore size of 300 Å.

18. Process according to claim 8 wherein the matrix is a polymer carrying a ligand wherein the ligand is phenyl.

* * * * *